United States Patent
De Klerk-Engels et al.

(10) Patent No.: US 12,226,459 B2
(45) Date of Patent: Feb. 18, 2025

(54) COLLAGEN HYDROLYSATE FOR USE IN PREVENTION AND/OR TREATMENT OF POST INTENSIVE CARE SYNDROME (PICS)

(71) Applicant: ROUSSELOT B.V., Ghent (BE)

(72) Inventors: Barbara De Klerk-Engels, Ghent (BE); Elien Monique Gevaert, Ghent (BE); Praneeth Reddy Kuninty, Ghent (BE); Janne Prawitt, Ghent (BE); Nicolina Virgilio, Ghent (BE)

(73) Assignee: ROUSSELOT B.V., Ghent (BE)

( * ) Notice: Subject to any disclaimer, the term of this patent is extended or adjusted under 35 U.S.C. 154(b) by 0 days.

(21) Appl. No.: 18/695,013

(22) PCT Filed: Aug. 30, 2023

(86) PCT No.: PCT/EP2023/073847
§ 371 (c)(1),
(2) Date: Mar. 25, 2024

(87) PCT Pub. No.: WO2024/047134
PCT Pub. Date: Mar. 7, 2024

(65) Prior Publication Data
US 2024/0415938 A1 Dec. 19, 2024

(30) Foreign Application Priority Data
Aug. 31, 2022 (BE) .................................. 2022/5691

(51) Int. Cl.
| A61K 38/39 | (2006.01) |
| A61K 9/14 | (2006.01) |
| A61K 38/01 | (2006.01) |
| A61P 43/00 | (2006.01) |
| C07K 14/78 | (2006.01) |

(52) U.S. Cl.
CPC ............... *A61K 38/39* (2013.01); *A61K 9/14* (2013.01); *A61K 38/01* (2013.01); *A61K 38/014* (2013.01); *A61P 43/00* (2018.01); *C07K 14/78* (2013.01); *A23V 2250/5422* (2013.01); *A23V 2250/55* (2013.01)

(58) Field of Classification Search
CPC ...... A61K 38/39; A61K 38/014; A61K 38/01; A61K 38/012; C07K 14/78; A23V 2250/55; A23V 2250/5422
See application file for complete search history.

(56) References Cited

U.S. PATENT DOCUMENTS

| 2012/0141448 A1* | 6/2012 | De Ferra ................ A61K 38/28 514/5.1 |
| 2015/0232534 A1* | 8/2015 | Oesser .................... A23J 3/342 435/68.1 |
| 2022/0295854 A1* | 9/2022 | Feige ...................... A23L 33/18 |

FOREIGN PATENT DOCUMENTS

| CN | 113271961 A | 8/2021 |
| JP | 2019-112361 A | 7/2019 |
| JP | 2019-529365 A | 10/2019 |
| WO | 2020/245299 A1 | 12/2020 |

OTHER PUBLICATIONS

Colbenson et al. Post-intensive care syndrome: impact, prevention, and management. Breathe 15(2): 98-101, 2019.*
Miyab et al. The effect of a hydrolyzed collagen-based supplement on wound healing in patients with burn: A randomized double-blind pilot clinical trial. Burns 46: 156-163, 2020.*
Rawal et al. Post-intensive care syndrome: an overview. J Translation Int Med 5(2): 90-92, 2017.*
Japanese Office Action for Patent Application No. 2024-519454, dated Aug. 30, 2024, pp. 1-5 (Translation Included).
Chinese Office Action for Patent Application No. 202380013782.X, dated Jul. 26, 2024, pp. 1-18 (Translation Included).
International Search Report and Written Opinion for WO 2024/047134 (PCT/EP2023/073847), dated Nov. 8, 2023, pp. 1-15.
BE Search Report for BE2022/5691, dated Apr. 24, 2023, pp. 1-11.
Denise Zdzieblik et al: "Collagen peptide supplementation in combination with resistance training improves body composition and increases muscle strength in elderly sarcopenic men: a randomised controlled trial", British Journal of Nutrition, vol. 114, No. 8, Oct. 28, 2015 (Oct. 28, 2015), pp. 1237-1245.
Marra Annachiara et al: "The ABCDEF Bundle in Critical Care", Critical Care Clinics, vol. 33, No. 2, Apr. 1, 2017 (Apr. 1, 2017), pp. 225-243.
Leon-Lopez Arely et al.: "Hydrolyzed Collagen-Sources and Applications", Molecules vol. 24, No. 22 Nov. 7, 2019 (Nov. 7, 2019), p. 4031.
Chinese Office Action for Patent Application No. 202380013782.X, dated Oct. 31, 2024, pp. 1-10 (Translation Included).
Jiang Xirui, Novel Biotechnological Fermentation Products, first edition, China Light Industry Press, Aug. 2020, page 331. (Translation not available).
Hong Hui, Collagen and Collagen Peptides Function and Application, first edition, China Light Industry Press, Jan. 2022, page 4. (Translation not available).

* cited by examiner

*Primary Examiner* — Bridget E Bunner

(74) *Attorney, Agent, or Firm* — Thomas| Horstemeyer, LLP

(57) ABSTRACT

The present invention relates to a use of collagen hydrolysate after intensive care unit (ICU) stay. The collagen hydrolysate improves the recovery and prevents and/or treats post intensive care syndrome (PICS) after ICU stay. The collagen hydrolysate is preferably administered as a supplement in the context of ICU stay and/or PICS. Collagen hydrolysate is generally-accepted to be safe and therefore can be taken as a preventive and long-term measure.

10 Claims, 3 Drawing Sheets

Figure 1:
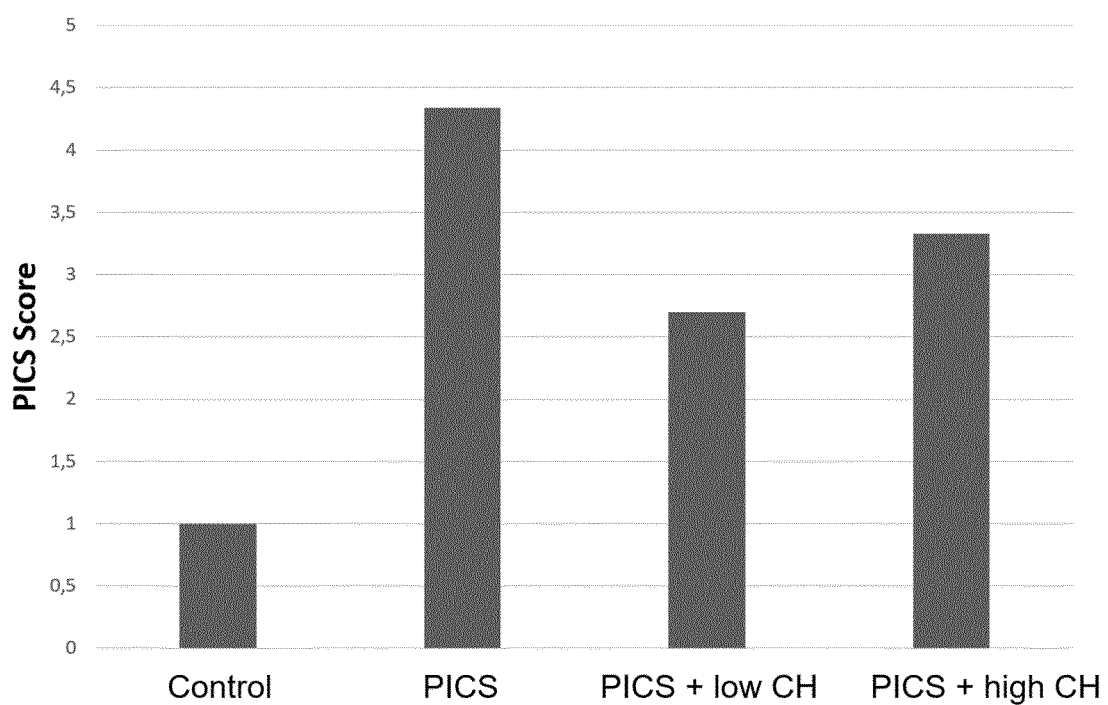

COLLAGEN HYDROLYSATE FOR USE IN PREVENTION AND/OR TREATMENT OF POST INTENSIVE CARE SYNDROME (PICS)

CROSS-REFERENCE TO RELATED APPLICATIONS

This application is the National Stage of International Application No. PCT/EP2023/073847, filed Aug. 30, 2023, which claims priority to BE2022/5691, filed Aug. 31, 2022, all of which are entirely incorporated herein by reference.

TECHNICAL FIELD

The current invention relates to a strategy for prevention and/or treatment of post intensive care syndrome (PICS), in particular to a supplement for prevention and/or treatment of PICS.

BACKGROUND OF THE INVENTION

Intensive care unit (ICU) survivors typically may suffer from various (serious) impairments as a result of ICU hospitalization. Post intensive care syndrome (PICS) is a medical condition that can arise after a patient is hospitalized at the ICU and is associated with characterizing, persisting changes in physical, cognitive and mental health status (Needham et al. Crit Care Med 2012; 40: 502-509). The complaints due to PICS may persist for weeks to years after the ICU stay. PICS patients may experience lasting deficits in memory and concentration, depression and anxiety. Furthermore, PICS patients as may be unable to work or participate in social gatherings. As a result, the quality of life in PICS patients is generally drastically impaired (Schweickert et al. Lancet. 373 (9678): 1874-1882).

Several factors may contribute to the development of PICS, although it is generally accepted that the acute complications of ICU hospitalization (e.g. mechanical ventilation, immobilization and deep sedation) are risk factors for developing the long-term symptoms constituting PICS. It is generally considered that the chance of developing PICS is associated with the time spent at the ICU. Most typically, the chance of developing PICS significantly increases for ICU stay of 48 h or more. Although the mechanisms are currently not exactly understood, the different aspects of PICS may have one or more common causes, despite possible heterogeneity in symptoms. The PICS symptoms may be subtle at first, and consequently not readily recognized by the patient and the clinician. The symptoms may progress and result in chronic symptoms months to even years following ICU hospitalization (Colbenson et al. Breathe 2019 15: 98-101).

Different measurement instruments have been reported to diagnose PICS (Yuan et al. Nurs Crit Care. 2022 January; 27(1):8-9), but a particularly appealing and practical one is the Post-Intensive Care Syndrome Questionnaire (PICSQ). The PICSQ is an 18-item self-reported measurement tools encompassing the physical, cognitive, and psychological domain. It was shown that the PICSQ is a reliable and consistent tool to diagnose PICS in ICU survivors (Jeong et al. Intensive Crit Care Nurs. 2019 December;55:102756).

To date, there is no effective therapy for PICS. Instead, the American College of Critical Care Medicine and the Society of Critical Care Medicine focuses on the following pillars to prevent PICS (Marra et al. Crit Care Clin 2017; 33: 225-243):

(1) the correction or removal of causative factors;
(2) the administration of anxiolytic and antipsychotic agents;
(3) reduction of sources of environmental stress; and
(4) frequent patient and family communication.

As can be seen, there currently are no adequate measures that can effectively prevent or treat PICS. Instead, current strategies aim to reduce one or more symptoms of PICS, but do not seem to relieve the medical condition PICS itself or the underlying (common) cause. Furthermore, anxiolytic and antipsychotic agents cause side effects and are therefore preferably avoided. In addition, current treatment of (symptoms) of PICS is time-consuming and complex, i.e. necessitating different therapeutic interventions in parallel, which put an additional burden on the patient.

There remains an unmet need for an effective strategy to prevent and/or treat PICS. In particular, there is a desire for a strategy that is considered to be safe and therefore can be taken as long-term (preventive) measure. The present invention aims to provide a solution for this.

SUMMARY OF THE INVENTION

The inventors surprisingly found that collagen hydrolysate improves recovery after intensive care unit (ICU) stay and prevents and/or treats post intensive care syndrome (PICS).

In one aspect, the present invention relates to a use of collagen hydrolysate after ICU stay.

In one aspect, the present invention relates to a use of collagen hydrolysate for improving the recovery after intensive care unit stay.

In one aspect, the present invention relates to collagen hydrolysate for use in prevention and/or treatment of PICS after ICU stay.

In one aspect, the present invention relates to a collagen hydrolysate, for use after ICU stay.

In one aspect, the present invention relates to a collagen hydrolysate, for use in a subject after ICU stay.

In one aspect, the present invention relates to a collagen hydrolysate, for use in a subject at risk of PICS after ICU stay.

DETAILED DESCRIPTION OF THE INVENTION

ICU Stay

The use of the invention pertains to administration of collagen hydrolysate after ICU stay and/or for improving recovery after ICU stay.

Use of collagen hydrolysate according to the invention solves the problem of subjects experiencing (long-term) symptoms after ICU stay and/or showing impaired recovery after ICU stay.

The term "after ICU stay" in the context of the current invention means any period of time, irrespective of the amount of time, counting from the moment that a subject leaves the ICU (and wherein subjects may develop symptoms of PICS). PICS most typically establishes within months until years after ICU stay, and the term "after ICU stay" typically means within weeks to years (most typically within 2 years) after ICU stay. The term "after ICU stay" is not limited to any time period, in case a subject is diagnosed with PICS (i.e. associated with the ICU stay) and/or at least one symptom thereof, or diagnosed with increased risk of developing PICS.

The chance of developing PICS is associated with the time spent at the ICU. PICS is most typically seen for an ICU stay of 48 h or more. In an embodiment, the collagen hydrolysate of the current invention is for use in subjects that have stayed at the ICU for at least 24 h, preferably at least 48 h, more preferably at least 72 hours, even more preferably at least 7 days or 14 days.

It was found that early administration of collagen hydrolysate is advantageous to prevent and/or treat PICS after ICU stay. It may be even more advantageous to initiate the administration of collagen hydrolysate already during ICU stay or when entering the ICU, for example to further minimize the chance of developing PICS.

In an embodiment, the current invention pertains to administration of collagen hydrolysate to a subject entering or staying at the ICU. The collagen hydrolysate administered to a subjecting entering and/or staying at the ICU is preferably formulated as a food for special medical purpose (FSMP). The term "food for special medical purpose (FSMP)" means a regulated foodstuff to feed subjects for special medical purposes and/or subjects which have nutritional needs that cannot be met by consuming standard foodstuffs. In the case of ICU stay, administration of collagen hydrolysate (as FSMP) may typically be provided as (enteral) tube feeding, oral nutritional supplement, and/or administered intravenously.

PICS most typically is diagnosed within several months (e.g. onset 3-9 months after ICU stay) until years (typically within 2 years) after the ICU stay. When the collagen hydrolysate is administered as a preventive measure in the context of the current invention, it is preferred to start the administration before the moment PICS is normally diagnosed or experienced. Accordingly, it may be preferred to start collagen hydrolysate use or administration early on (e.g. days to weeks) after the leave from the ICU, or even during or immediately after ICU stay.

It was found advantageous when collagen hydrolysate administration is started within 3 weeks after the ICU stay. In a preferred embodiment, the dosage regimen for collagen hydrolysate comprises administration of collagen hydrolysate (starting) within 3 weeks, preferably (starting) within 2 weeks, more preferably (starting) within 1 week (e.g. within 6 days, or 5 days, or 4 days, or 3 days, or 2 days, or 1 day, or immediately) after ICU stay and/or at the moment leaving the ICU.

In an embodiment, the stay at the ICU is for one or more:
infection, preferably sepsis and/or COVID-19 (i.e. due to a SARS-CoV-2 infection);
surgery;
trauma;
(severe) inflammation;
respiratory failure;
myocardial infarction;
stroke;
hypoxemia; and
hypoglycemia.

In an embodiment, the current invention relates to a use of collagen hydrolysate for improving non-therapeutic or therapeutic-recovery after ICU stay.

The term "improving the recovery after ICU stay" in the context of the current invention encompasses one or more of: decreasing the time to resume work or school, decreasing the time to resume performing exercise, or decreasing the time to resume to self-care (i.e. not necessitating support from a healthcare professional in daily life). In addition or alternatively, the "improving the recovery after ICU stay" encompasses improving quality-of-life (QOL) level, preferably by comparing to a reference population experiencing PICS but that do not receive collagen hydrolysate or another known effective treatment for PICS. The reference values can be readily found in systematic reviews and the like (for example in the systematic review by Oeyen et al. Crit Care Med. 2010; 38(12):2386-2400). The QOL is preferably determined with a well-known QOL assessment tool in the field such as the Medical Outcomes Study 36-Item Short Form (SF-36) health survey, the Nottingham Health Profile (NHP), the Sickness Impact Profile (SIP), the Dartmouth Primary care Cooperative Information Project (COOP) Charts, the Quality of Well-Being (QWB) Scale, the Health Utilities Index (HUI), or the EuroQol Instrument (EQ-5D). In addition or alternatively, the term "improving the recovery after ICU stay" encompasses reducing the chance of developing one or more conditions related to ICU stay, such one or more of, preferably two or more of, most preferably all three of a physical condition (i.e. physical symptom, preferably a physical condition in PICS), a mental condition (i.e. mental symptom, preferably a mental condition in PICS), and a cognitive condition (i.e. cognitive symptom, preferably a cognitive condition in PICS).

The term "exercise" as used herein means any physical activity that can be planned, structured, and repetitive and has as a final or an intermediate objective. The term "exercise" as used herein typically has as goal the improvement or maintenance of physical fitness. For example, "exercise" may include all professional or non-professional activities including: sports, strength or resistance training, and endurance or aerobic activities. In addition or alternative, "exercise" may include endurance training. The term endurance training generally refers to training the aerobic system as opposed to the anaerobic system, e.g. by performing physical exercise at an increased heart rate for a prolonged period of time (e.g. at 70% maximum heart rate (MHR) for at least 30 minutes), for example during walking, running, jogging, cycling, swimming, rope jumping etc. The term "exercise" in the context of the current invention encompasses physical activities that can be performed by non-athletes, including but not limited to walking or hiking, dancing, swimming, water aerobics, jogging or running, aerobic exercise, yoga, cycling, or gardening (such as raking and pushing a lawn mower).

The use of collagen hydrolysate in the context of the current invention is preferably therapeutic. In certain embodiments, the use may be non-therapeutic. The subjects necessitating therapeutic or non-therapeutic treatment can be separated based on the nature of the ICU stay, the recovery thereafter, and/or whether the subject is at risk of developing one ore more pathological symptoms (of PICS) after ICU stay.

The subjects that benefit from non-therapeutic use of collagen hydrolysate are characterized by the absence of a pathology after ICU stay and therefore have no therapeutic benefit from the treatment with collagen hydrolysate. For example, this can be the case when the ICU uptake does not/is not expected to lead to health issues, symptoms of pain, or suffering. In addition or alternatively, this can be the case if the ICU stay has a nature or severity such that the subject is expected to naturally recover without intervention, but when it is nevertheless advantageous to shorten the time to recovery. Non-therapeutic use can also mean that the collagen hydrolysate improves the general performance of an otherwise healthy subject (i.e. having no PICS or other pathology), such as by achieve one or more of the following effects:
improving aesthetic or cosmetic appearance of the body (e.g. body weight increase towards more desirable body weight);

increasing productivity in daily life, such as by providing more energy, stamina, endurance, or physical capacity;
improving general functioning and/or well-being;
improving concentration;
reducing anxiety;
improving sleep.

In case of doubt, the professional medical practitioner is able to determine on a case-by-case basis whether following ICU stay a therapeutic or a non-therapeutic intervention is needed (i.e. whether a person falls in the group of healthy subjects or in the group of pathological subjects). The professional medical practitioner may for instance establish whether (the nature of and/or duration of the) ICU stay will lead to health and psychological risks.

PICS

The use of the invention preferably pertains to a prevention and/or treatment of PICS after ICU stay.

The present inventors found that collagen hydrolysate administration effectively prevents and/or treats PICS. It was surprisingly found that collagen hydrolysate outperforms agents that are known to target specific physical, cognitive, or mental symptoms seen in PICS, including fluoxetine (an antidepressant) or whey protein (a muscle promotor). This suggests that known strategies to treat physical, cognitive, or mental symptoms are inadequate for treating PICS. Instead, collagen hydrolysate supplementation appears to combat the underlying cause of PICS and the pathophysiology of PICS itself, rather than (only) the symptoms. Several common features can be seen in PICS patients, which suggests that symptoms of PICS have a common underlying disease. Without being bound by theory, it appears that collagen hydrolysate supplementation plays a role in one or more of limiting excessive stem cell activation, ameliorating epithelial barrier dysfunction, limiting, epithelial-mesenchymal transition, and limiting fibrosis and inflammation.

In the context of PICS, administration of collagen hydrolysate appears to treat and/or prevent the pathophysiology of PICS itself, alternatively or in addition to treating and/or preventing the symptoms.

The use of collagen hydrolysate in prevention and/or treatment of PICS offers the advantage/benefit that collagen hydrolysate, also following frequent administration (e.g. as a (daily) supplement) is generally recognized as safe (GRAS). In comparison, anxiolytic and antipsychotic drugs used in the treatment of PICS are frequently associated with side effects and are therefore undesirable. Moreover, there may be hesitancy to use such drugs in the early stage of PICS, i.e. when symptoms are subtle and not yet fully recognized. ICU survivors benefit greatly from a prophylactic measure with collagen hydrolysate, because it can be taken early on after leaving the ICU (or even when entering or during ICU stay) to more effectively prevent PICS.

The use of collagen hydrolysate in prevention and/or treatment of PICS solves the problem that there is no single method yet that may simultaneously ameliorate different aspects of PICS and/or target the underlying pathophysiology of PICS (i.e. the condition PICS itself). The strategies in the prior art aim to combat the different symptoms of PICS, which is generally less efficient and effective. Collagen hydrolysate administration seems to treat or remove the underlying cause of PICS and the pathophysiology of PICS itself.

Regarding the diagnosis of PICS, there may be no single-applied measure for PICS adopted by professional medical practitioners or healthcare institutes. Instead, professional medical practitioners or health centres may (and tend to) use their own measurement instrument(s) for PICS. Such measurement systems generally involve a combination of measurement systems spanning the physical, cognitive, and mental area's in PICS. In the context of the current invention, the presence of PICS may be defined according to any one of the local practices (i.e. professional medical practitioner or health care institute as), preferably the local practice of the healthcare centre of the ICU stay. In the current disclosure, a subject is considered to have PICS when diagnosed as such by a professional healthcare professional responsible for the diagnosis and/or treatment of PICS and/or conditions or symptoms related to (prolonged) ICU hospitalization. In addition or alternatively, a subject is considered to have PICS when experiencing two or more PICS symptoms as disclosed herein. In addition or alternatively, a subject to be treated in the context of the current invention may be at risk of experiencing PICS or PICS-related symptoms, such as when experiencing poor recovery after ICU stay, experiencing early signs of PICS, and/or risk factors increasing the chance of establishing PICS. The chance of developing PICS increases drastically following ICU hospitalization for three days or more. Therefore, in an embodiment, a subject to be treated in the context of the current invention is a subject who has stayed at the ICU for three days or more, e.g. to prevent PICS from occurring when at high risk of developing it.

A preferred method of diagnosing PICS in the context of the current invention is the PICS Questionnaire (PICSQ), as reported by Jeong et al. (Intensive Crit Care Nurs. 2019 December;55:102756). PICSQ exists of 3 factors (mental, cognitive and physical area's) and 18 items and is shown to be a valid and reliable tool to establish PICS in a simple and relatively quick way. The 18 items (Table 4 in Jeong et al, herein incorporated by reference) are assigned a score by the subject of 0 (Never), 1 (Sometimes), 2 (Most often), or 3 (Always). The total PICSQ score can be between 0 and 54. In the context of the current invention, a subject has PICS if the PICSQ score is 20 or higher (mild PICS) or 30 or higher (average PICS) or 40 or higher (severe PICS). In an embodiment, a "reduction", "amelioration" or "treatment" of PICS means that the PICSQ score is reduced to below 20 points. In an embodiment, a "reduction", "amelioration" or "treatment" of PICS means that the PICSQ score is decreased by at least 10 points, preferably at least 20 points, more preferably at least 30 points (such as compared to a control not receiving treatment and/and/or when comparing the PICSQ score before and after treatment with the collagen hydrolysate of the invention).

In addition or alternatively, in the context of the current invention, a subject has PICS when experiencing at least one, preferably at least two, most preferably at least all three of a physical condition, a mental condition and a cognitive condition, and which is associated with ICU stay, preferably ICU stay for at least 48 h.

The physical condition as disclosed herein is preferably one or more of a decrease in muscle strength, a decrease in exercise tolerance, and a decrease in motor coordination.

The mental condition as disclosed herein is preferably one or more of anxiety, depression and posttraumatic stress disorder.

The cognitive condition as disclosed herein is preferably one or more of a decrease in memory and a decrease in concentration.

The decrease in the physical, mental or cognitive condition are preferably determined relative to the moment before ICU stay and/or the (highest) value after ICU stay. In addition, the physical, mental or cognitive condition can be compared to normative data, e.g. in a healthy population (such as reported in a systematic review and the like).

The "muscle strength" as used herein is preferably established as reduction of two or more of handgrip strength (Jamar dynamometer), muscle strength leg [HHD (i.e. Handheld dynamometry) quadriceps muscle], and muscle strength arm (HHD biceps brachii muscle), which are each well-known tests in the field and which the skilled person is familiar with.

The "exercise tolerance" (i.e. exercise capacity) as used herein is preferably established with the 6-minute walk distance (6MWD) test, which is a well-known test in the field. Preferably, the 6MWD is performed in a corridor (minimal 30 meters) and the measured values will be compared to normative data as reported by Gibbons et al. (J Cardiopulm Rehabil.2001; 21(2):87-93).

The "motor coordination" as used herein is preferably established with the Kiphard-Schilling body coordination test (KTK), which is a well-known test in the field. Based on the four items of the KTK, the "motor quotient" (MQ) can be determined, i.e. a global indicator of motor coordination adjusted for age and gender (Popovic et al. Int J Environ Res Public Health. 2020 August; 17(16): 5902. Impaired motor coordination is considered if the MQ is 71-85 (moderately impaired) or 56-70 (severely impaired).

The "anxiety" as used herein is preferably established with the Generalized Anxiety Disorder Scale-7 (GAD-7). Anxiety is considered if the GAD-7 score is 5-9 (mild anxiety), 10-14 (moderate anxiety), or 15-21 (severe anxiety), using the scoring system as disclosed in FIG. 1 in Spitzer et al. (Arch Intern Med. 2006 May 22;166(10):1092-7) herein incorporated by reference.

The "depression" as used herein is preferably established with the Depression items in the Hospital Anxiety and Depression Scale (HADS), which is a well-known test in the field. Depression is considered if the Depression items in the HADS score (i.e. total score of 21) score 8-10 (borderline case) or 11-21 (abnormal), using the scoring system as disclosed in FIG. 1 in Richi et al. (Indian J Ophthalmol. 2017 November; 65(11): 1203-1208) herein incorporated by reference.

The "posttraumatic stress disorder" as used herein is preferably established with the PCL-5, which is a 20-item self-report measure that assesses the 20 DSM-5 symptoms of posttraumatic stress disorder, which is a well-known test in the field. Posttraumatic stress disorder is considered if the total score (of 80 in total) is 33 or higher.

The "memory" or "concentration" as used herein is preferably established with the 30-point Montreal Cognitive Assessment (MoCA) test, which is a well-known test in the field. Memory or concentration is considered deficient for a score of 20-25 (mild impairment), or 19 or lower (high impairment).

In a preferred embodiment, the current invention relates to collagen hydrolysate for use in treatment of a subject experiencing one or more, preferably two or more symptoms, most preferably three symptoms of PICS, wherein the two or more symptoms are preferably from a different PICS domain (i.e. physical domain, mental domain cognitive domain) as disclosed herein.

In an embodiment, the collagen hydrolysate is for use in ameliorating at least one, preferably two, most preferably all of:
- a physical condition (i.e. physical symptom), preferably a physical condition in PICS;
- a mental condition (i.e. mental symptom), preferably a mental condition in PICS;
- a cognitive condition (i.e. cognitive symptom), preferably a cognitive condition in PICS.

Collagen Hydrolysate of the Invention

The term "collagen hydrolysate" in the context of the current invention means a mix of short chains of amino acids (di-, tri, oligopeptides, polypeptides) derived from (partial) hydrolysis from native (full-length) collagen. The degree of hydrolysis, which is preferably enzymatic hydrolysis, has an impact on the average molecular weight (expressed in Dalton, Da) of the final product. The term "collagen hydrolysate" may be used interchangeably and synonymous with the terms "hydrolysed collagen" or "collagen peptide". The "collagen hydrolysate" in the context of the current invention encompasses collagen which is subjected to hydrolysis or partial hydrolysis.

The "collagen hydrolysate" herein is preferably produced from a collagen-containing material in a one-step process or via the intermediate gelatin stage (i.e. thus "hydrolysed gelatin" is obtained). The terms "collagen hydrolysate" and "hydrolysed gelatin" can be used interchangeably in the context of the current invention. The term "gelatin" as used herein means an irreversible form of collagen as obtained by partial hydrolysis of collagen, wherein the partial hydrolysis reduces protein fibrils of collagen into smaller peptides. Depending on the process used, two types of gelatin are generally obtained, namely type A (acid hydrolysis) and type B (alkaline hydrolysis). In the context of the current invention, the "gelatin" preferably is either Type A or Type B gelatin. Depending on the physical and chemical methods of the partial hydrolysis, the molecular weight of the peptides falls within a broad range (typically 15-40 kDa). The partial hydrolysis provides the gelatin with the ability to hold water and the gelling capacity. The term "hydrolysed gelatin" in the context of the current invention means a product obtained by the (partial) hydrolysis of gelatin and which leads to a (further) mixture of peptides and lower molecular weight of the gelatin. Hydrolysed gelatin, among others, distinguishes from gelatin in terms of gelling capacity and/or molecular weight (e.g. gelatin having a bloom strength of 30 or lower and/or a molecular weight of 10 kDa or larger, preferably 15 kDa or larger), wherein hydrolysed gelatin has no/little gelling capacity (preferably a bloom strength below 30) and/or a lower molecular weight (preferably below 15 kDa, more preferably below 10 kDa). The "gelatin" may be hydrolysed by acids (hydrogen ions), i.e. to obtain "acid-hydrolysed gelatin". The "gelatin" may be hydrolysed by alkali (hydroxyl ions), i.e. to obtain "alkali-hydrolysed gelatin. The "gelatin" may be hydrolysed by one or more enzymes (e.g. pepsin, trypsin), i.e. to obtain "enzyme-hydrolysed gelatin". In all cases, the reaction consists in the rupturing of one or more of the peptide link with the addition of 1 molecule of water.

The collagen hydrolysate in the context of the current invention may be derived from one or more types of collagen selected from collagen types I-XXVII, preferably one or more of type I, II, III, V, or X collagen, more preferably one or more of type I, II or III collagen. In addition or alternatively, the collagen hydrolysate as disclosed herein may be a mixture of two or more types of collagen, preferably two one or more of type I, type II, and type III collagen.

The collagen as disclosed herein may be derived from any one or more animals or species of animals, such as bovine (species), pig (species), chicken and fish (species).

In an embodiment, the collagen is derived from a cow. In an embodiment, the collagen as is derived from a pig. In an embodiment, the collagen is derived from a fish. In an embodiment, the collagen is derived from a chicken. In various embodiments, the collagen is a mixture of collagen from different sources, such as collagen originating from multiple animal species and/or collagen originating from different tissues. For example, the collagen as disclosed herein may be a mixture of two or more collagens chosen from the group consisting of fish collagen, porcine collagen, chicken collagen, and bovine collagen.

It may be most advantageous in the context of the current invention to use porcine collagen hydrolysate, as in the context of the current invention it may have the highest bioavailability and/or bioactivity (compared to fish and bovine collagen hydrolysate, among others). Porcine collagen hydrolysate putatively leads to highest effectiveness on prevention and/or treatment of PICS.

In a preferred embodiment, the collagen as disclosed herein is porcine collagen and/or the collagen hydrolysate as disclosed herein is derived from hydrolysis of porcine collagen.

The collagen in the context of the current invention may be derived from one or more tissues selected from the group consisting of skin, scale, antler, protrusions (e.g. humps) horns, head, brain, neck, ear, eye, nose, tongue, lip, mouth, oesophagus, trachea, sternum, larynx, bronchi, limbs, feet, toes, palms, claws, bones, cartilage, bone marrow, joints, membranes, hind, ligaments, tendon, rib, diaphragm, muscle, skeletal muscle, smooth muscle, intestine, blood vessels, bladder, stomach, aorta, heart, liver, kidney, chest, lung, spleen, pancreas, egg, sperm, testis, ovary, nerve, gallbladder, and belly. The term "skin" as disclosed herein encompasses "hide", i.e. meaning the outer covering of large animals such as from bovine (species) or any other large animals. The terms "skin" and "hide" may herein be used interchangeably, and may refer the outer coverage of an animal, irrespective of size.

In a preferred embodiment, the collagen as taught herein is derived from skin and/or skin connective tissue. In preferred embodiment, the collagen as taught herein is derived from cartilage. In a preferred embodiment, the collagen as taught herein is derived from bone. In a preferred embodiment, the collagen as taught herein is derived from sternum.

The collagen as disclosed herein may be a mixture of collagens derived from two or more tissues and/or two or more animals. In an embodiment, the collagen as disclosed herein is a mixture of two or more collagens selected from the group consisting skin collagen, cartilage collagen, sternum cartilage and bone collagen.

In various embodiments of the current invention, the collagen hydrolysate may be produced by the enzymatic hydrolysis or partial enzymatic hydrolysis of collagen, wherein the enzyme used for this purpose may be one or more selected from the group consisting of serine protease, alkaline protease, neutral protease, flavor protease, complex protease, thiol protease, bromelain, metalloprotease, aspartame, protease, carboxypeptidase, pepsin, chymotrypsin, trypsin, cathepsin K, chymotrypsin, papain, and subtilisin.

The collagen hydrolysate in the context of the current invention may have an average molecular weight of at least 300 Da, 400 Da, 500 Da, 1000 Da, 1500 Da, 1600 Da, 1700 Da, 1800 Da, 2000 Da, 2100 Da, 2200, Da 2500 Da, 3000 Da, 3500 Da, 4000 Da, 4500 Da, 5000 Da, 5500 Da, 6000 Da, 6500 Da, 7000 Da, 7500 Da, 8000 Da, 8500 Da, 9000 Da, 9500 Da, or 10000 Da. In addition or alternatively, the collagen hydrolysate in the context of the current invention may have an average molecular weight of no more than 10000 Da, 9500 Da, 9000 Da, 8500 Da, 8000 Da, 7500 Da, 7000 Da, 6500 Da, 6000 Da, 5500 Da, 5000 Da, 4500 Da, 4000 Da, 3500 Da, 3000 Da, 2500 Da, 2100 Da, 2000 Da, 1800 Da, 1700 Da, 1600 Da, 1500 Da, 1000 Da, 500 Da, 400 Da, or 300 Da.

In a preferred embodiment, the collagen hydrolysate of the invention has an average molecular weight of 1000-9000 Da. In an embodiment, the collagen hydrolysate of the invention has an average molecular weight of less than 5000 Da. In an embodiment, the collagen hydrolysate of the invention has an average molecular weight of 1400-2200 Da, more preferably 1600-2000 Da. In an embodiment, a collagen hydrolysate is used derived from porcine collagen and having a molecular weight below 5000 Da (e.g. 1400-2200 Da).

It is considered that amelioration of PICS can be achieved with collagen hydrolysates from different sources and in a wide range of molecular weights, e.g. at least in the range of 1000-9000 Da (which is typical for collagen hydrolysates). The proof that different collagen hydrolysates can be suitable for ameliorating PICS was found by executing a study with the aim to investigate the single-dose bioavailability of collagen hydrolysate from different sources (bovine, fish and porcine) and of different mean molecular weight (2000 Da and 5000 Da for bovine collagen hydrolysate). The study showed that the uptake of collagen hydrolysates in blood appears similar for collagen hydrolysates from the sources porcine, bovine and fish and also for hydrolysates with a relatively high average molecular weight (5000 Da) and relatively lower average MW (2000 Da).

It may be most advantageous in the context of the current invention to use collagen hydrolysate with relative low molecular weight, e.g. below 5000 Da, and more preferably an average molecular weight of 1400-2200 Da, even more preferably 1600-2000 Da. A relatively low molecular weight in the context of the current invention appears to be associated with the highest bioavailability and/or bioactivity. Collagen hydrolysate with a relatively low molecular weight putatively leads to highest effectiveness on prevention and/or treatment of PICS.

The molecular weight of the collagen hydrolysate appears to play a role in improving recovery after ICU stay and/or the amelioration of PICS. A relatively low molecular weight, e.g. below 5000 Da and preferably within the 1400-2200 Da range, appears to be most effective.

In a preferred embodiment, the collagen hydrolysate of the invention has an average molecular weight of less than 5000 Da.

In a preferred embodiment, the collagen hydrolysate of the invention has an average molecular weight of 1400-2200 Da, more preferably 1600-2000 Da.

In a particular embodiment, it is preferred in the context of the current invention to use a collagen hydrolysate derived from porcine collagen and having a molecular weight below 5000 Da (e.g. 1400-2200 Da).

The average molecular weight as disclosed herein is preferably the weight average molecular weight.

A suitable and preferred method of measuring the molecular weight of the collagen hydrolysate is by high performance size-exclusion chromatography (HP-SEC), e.g. after treating the samples with collagen hydrolysate with a sodium acetate-ethanol solution to precipitate the protein-poor fraction (including glycosaminoglycans) and using the protein-rich fraction (supernatant) for HP-SEC of the collagen hydrolysate. In addition or alternatively, a preferred method of determining the collagen hydrolysate molecular weight is according to Edgar et al. (Sci. Rep. 2018 Jul. 11;8(1):10474).

Formulations

The collagen hydrolysate as disclosed herein may be provided in a food formulation, food supplement formulation, or pharmaceutical formulation, preferably a food supplement formulation.

In an embodiment, the collagen hydrolysate of the invention is provided in one or more formulations selected from the group consisting of a drinkable solution or suspension, drink such as syrup, artificially-flavoured drink, carbonated beverage, beer, tea, (water-soluble) powdered mixture, (water-soluble) paste, (water-soluble) powder, (water-soluble) tablet, (water-soluble) pill, (water-soluble) dragee, (water-soluble) caplet, (water-soluble) sachet, or (water-soluble) capsule. In addition or alternatively, the collagen hydrolysate as taught herein may be present in a functional food such as a juice, shake, dairy drink, yoghurt, yoghurt drink dessert, energy bar, nutritional bar, slimming bar, confectionery such as gummies or centre-filled gummies, candies or chocolate pastilles.

In an embodiment, preferably in the context of administration in a hospital setting or at the ICU, the collagen hydrolysate is provided as a food for special medical purpose (FSMP)_ and/or as (enteral) tube feeding or oral nutritional supplement. In an embodiment, preferably in the context of administration in a hospital setting or at the ICU, the collagen hydrolysate is administered intravenously.

In an embodiment, the collagen hydrolysate is provided in a liquid dosage form.

In an embodiment, the collagen hydrolysate is provided in a solid dosage form, preferably a capsule, a tablet, or a powder, preferably a powder.

Administration Regimens

In different embodiments, the unit dose and/or daily dose of the collagen hydrolysate as disclosed herein is at least 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200, all in g. In addition or alternatively, in different embodiments, the unit dose and/or daily dose of the collagen hydrolysate as disclosed herein is no more than 200, 190, 180, 170, 160, 150, 140, 130, 120, 110, 100, 95, 90, 85, 80, 75, 70, 65, 60, 55, 50, 45, 40, 35, 30, 25, 20, 15, 10, 5, or 1, all in g.

The term "daily dose" in the context of the current invention means the total dry weight amount of a compound, substance or composition administered to a subject per day. The daily dose of may be administered as a single unit dose, or as two, three, four or more unit doses. The two or more unit doses may be equal or different in amount.

The term "unit dose" in the context of the current invention means an amount or unit of e.g. a compound, substance, or composition administered to/taken by a subject in a single dose. The unit dose may for example be in a pre-prepared form (e.g. prepacked dosage) ready for administration. The unit dose may for example (also) be identifiable from the product packaging or label. The total daily dose may be divided into multiple unit doses each having a reduced dose as compared to the total daily dose. The daily dose of the composition as disclosed herein is preferably administered as two unit doses, more preferably as two unit doses each corresponding to 30-70%, preferably 40-60% (e.g. 50%) of the daily dose amount.

The dose of collagen hydrolysate as disclosed herein is preferably based on the dry weight of collagen hydrolysate.

In a preferred embodiment, the use of collagen hydrolysate as disclosed herein comprises administering the collagen hydrolysate in a daily dose of 1-100 g, preferably 10-95 g, more preferably 20-90 g.

The recovery after ICU stay and/or amelioration of PICS was found to be most apparent following continuous daily administration of collagen hydrolysate, especially in combination with administration for at least 3 consecutive weeks.

It was seen in a clinical setting that after ingestion of collagen hydrolysate, the amino acids rapidly increase in the blood and reach a maximum level after approximately one hour. Thereafter, the amino acid levels decline close towards the baseline level over the course of several hours (e.g. 6-10 hours). Without being bound by theory, it appears that daily intake (or twice daily intake) of collagen hydrolysate leads to improved prevention and/or treatment of PICS by sustaining the amino acid profile in the blood and achieve highest bioactivity.

In an embodiment, the collagen hydrolysate is administered to a subject repeatedly, preferably at least once every day or at least once every other day.

In an embodiment, the collagen hydrolysate is administered to a subject for at least 2 consecutive weeks, preferably for at least 4 consecutive weeks or at least 5 consecutive weeks, more preferably for at least 6 consecutive week or at least 7 consecutive weeks, most preferably for at least 8 consecutive weeks.

It is found to be advantageous to administer the collagen hydrolysate within 3 weeks after the ICU stay. This is surprising, because PICS generally has a later onset, such as in the range of several months after the ICU stay. Without being bound by theory, early collagen hydrolysate administration may better target the underlying causes of PICS when administered already in an early stage.

In a preferred embodiment, the dosage regimen for collagen hydrolysate comprises administration of collagen hydrolysate (starting) within 3 weeks after intensive care unit stay, preferably (starting) within 2 weeks, more preferably (starting) within 1 week.

In several embodiments, the dosage regimen for collagen hydrolysate comprises administration of collagen hydrolysate (starting) within 12 weeks, or 11 weeks, or 10 weeks, or 9 weeks, or 8 weeks, or 7 weeks, or 6 weeks, or 5 weeks, or 4 weeks, or 3 weeks, or 2 weeks, or 1 week, or 6 days, or 5 days, or 4 days, or 3 days, or 2 days, or 1 day after ICU stay (after leaving the ICU).

The terms "administer" or "administration" in the context of the current invention mean providing a compound, substance, or composition to a subject consuming it. A subject consuming a compound, substance, or composition may administer it to himself/herself. In such a case the term "administer" can be read as "take in".

The term "subject" in the context of the current invention means any animal (e.g. a mammal), preferably a human. The term "subject" can be used interchangeably with "person" or "individual" in the context of the current invention. The "subject" can be a patient.

General Definitions

Reference to an element by the indefinite article 'a' or 'an' does not exclude the possibility that more than one of the elements is present, unless the context clearly requires that there be one and only one of the elements. The indefinite article 'a' or 'an' thus usually means 'at least one'.

The terms 'comprising' or 'to comprise' and their conjugations, as used herein, refer to a situation wherein said terms are used in their non-limiting sense to mean that items following the word are included, but items not specifically mentioned are not excluded. It also encompasses the more limiting verb 'to consist essentially of' and 'to consist of'.

The term "preventing" means to ensure that a subject will not develop a condition (e.g. PICS). An intervention is herein also considered to be a form of "preventing" when a condition is delayed, reduced in severity and/or reduced in incidence, even when the condition is not entirely kept from happening. In the context of the current invention, the terms "preventing" or "prevention" by an intervention encompasses the situation wherein a subject previously has experienced a condition (e.g. PICS) but an intervention keeps the condition from recurring.

The "preventing" or "prevention" may have a therapeutic and/or a non-therapeutic effect. If the "preventing" or "prevention" is therapeutic in nature, it may be also directed at a symptom of a disease or condition and/or an underlying pathology thereof. The "preventing", or "prevention" can be defined by any delay, change in severity, and/or change in incidence, such as of at least 5, 10, 20, 30, 40, 50, 60, 70, 80, 90, 100%, as compared to a control or reference as measured by any standard technique.

In the context of the current invention, "treating" means that an intervention reduces and/or cures a condition (e.g. PICS) once the condition is already existing. The "treating" may have a therapeutic and/or a non-therapeutic effect. If the "treating" is therapeutic in nature, it may be directed at a symptom of a disease or condition and/or an underlying pathology thereof. The treatment can for example be any reduction in severity, incidence, and/or frequency of the condition, such as of at least 5%, 10%, 20%, 40%, 50%, 60%, 80%, 90%, 95%, or completely (100%), as compared to a control or reference as measured by any standard technique.

The term "ameliorating" in the context of the current invention encompasses both the "preventing" and the "treating" of a condition. As used herein, "ameliorating" also encompasses "curing". The term "ameliorating" may in the context of the current invention be used interchangeably with "reducing" or "decreasing".

The terms 'to increase' and 'increased level' and the terms 'to decrease' and 'decreased level' (or to 'reduce" and "reduced level") preferably mean a change of at least 5%, such as at least 10%, 15%, 20%, 25%, 30%, 35%, 40%, 45%, 50% higher or lower, respectively than the corresponding level in control or reference. In addition or alternatively, a level in a sample may be increased or decreased when it is statistically significantly increased or decreased compared to a level in control or reference, irrespective of the size of the change.

The terms "consecutive" or "consecutively" used in the context of collagen hydrolysate administration means that the administrations follow one another in order without gaps in a given time period. For example, when "collagen hydrolysate is administered for 4 consecutive days", this means that the collagen hydrolysate is administered for at least once a day for 4 days in a row (e.g. on Monday, Tuesday, Wednesday, and Thursday of the same week), irrespective of the number of administrations per day or the total number of administrations. For example, when "collagen hydrolysate is administered for 4 consecutive weeks", this means that the collagen hydrolysate is administered for at least once a week for 4 weeks in a row, irrespective of the number of administrations per day, the number of administrations per week or the total number of administrations.

FIGURE LEGENDS

FIG. 1. PICS score in the "control", "PICS", "PICS+low dose CH" and "PICS+high dose CH" groups (mean).

Figure 2:
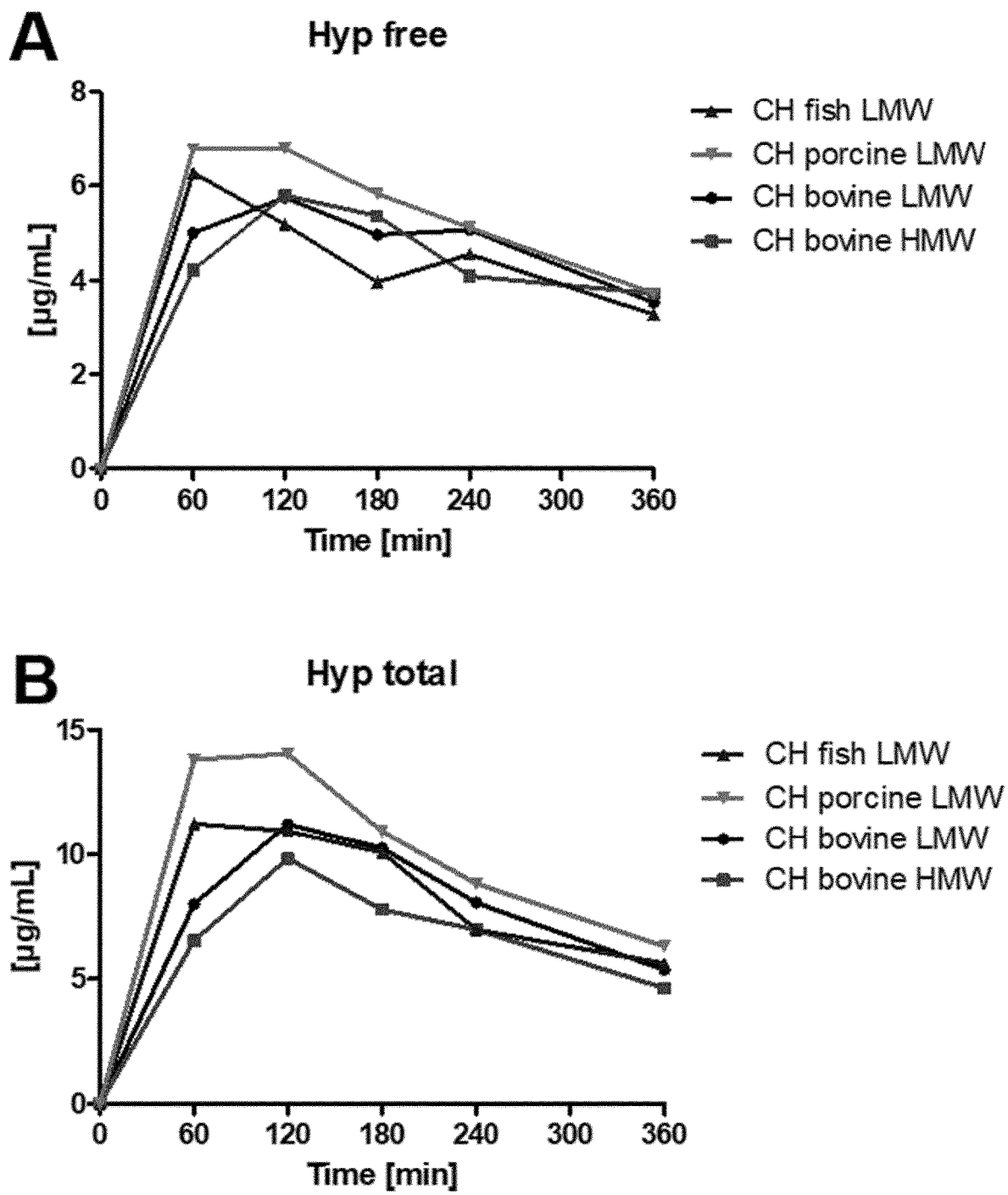

FIG. 2. Concentration-time curves of the free Hyp response [µg/mL] (A) or total Hyp response [µg/mL] (B) after intake of study products (mean, SD); n=6. CH=collagen hydrolysate; LMW=low molecular weight; HMW=high molecular weight.

Figure 3:
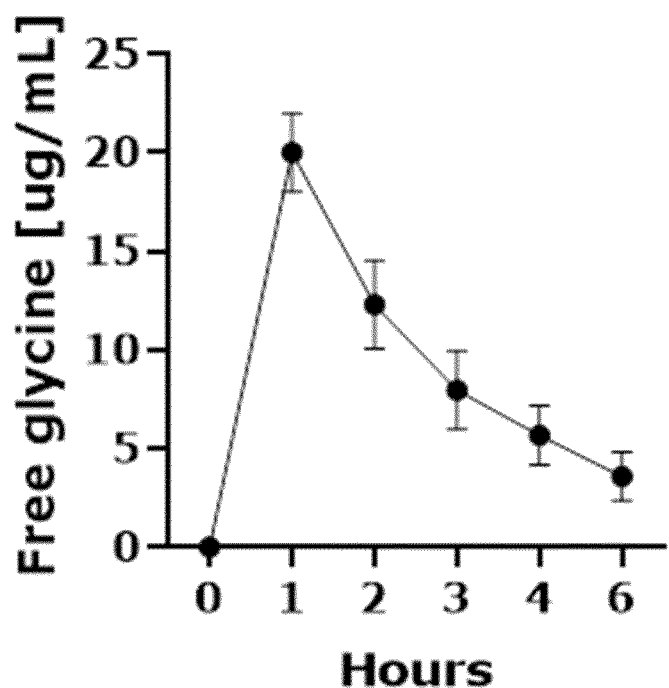

FIG. 3. Human plasma levels of free glycine before and after oral ingestion of porcine-based hydrolysed collagen (~1800 Da). Data are shown as mean+SEM (n=6).

EXAMPLES

Example 1: PICS Animal Study

Methods
Animal Model

A validated PICS mouse model was used, which is based on the model of Hujinami et al. (J Clin Med. 2021 April; 10(8): 1593.). The model is proven to induce PICS by mimicking ICU care following polymicrobial sepsis. This is achieved by intraperitoneal injection with cecal slurry followed by other typical ICU-related interventions (i.e. antibiotics and saline administration) for 72 h. The model incorporates a specific combination of physical (grip strength test), mental (anxiety level), and cognitive (discrimination index, habituation index, exploration time) parameters that often characterize PICS.

Pilot Study

The development of PICS in the model was first confirmed in a pilot study (not shown herein). The mice develop PICS after ~1 week.

The molecular weight (i.e. ~1800 Da) and source (porcine) of the collagen hydrolysate as used in this (full) comparative study is based on initial experiments comparing collagen hydrolysates of ~1800 Da and ~5000 Da and derived either from fish, bovine or porcine collagen sources. It was found that porcine collagen hydrolysate with relatively low molecular weight (<5000 Da, e.g. ~1800 Da) has the largest putative effect in ameliorating PICS.

Initial experiments showed that relatively early administration of collagen hydrolysate leads to most effective amelioration of PICS in the current model, as compared to delayed administration (delayed administration e.g. means starting from day 21 or later in the current model).

Treatment

The mice (C57BL6J, Charles River laboratories, France) receive collagen hydrolysate ("CH", Peptan, Porcine ~1800 Da, Rousselot B. V.) or the relevant controls according to the following experimental groups:
1. No PICS+vehicle (saline), i.e. "Control"
2. PICS+vehicle (saline), i.e. "PICS"
3. PICS+CH 1.8 g/kg (~10 g clinical dose), i.e. "PICS+ low dose CH"
4. PICS+CH 8 g/kg (~44 g clinical dose), i.e. "PICS+high dose CH"

The mice are administered once a day from day 12 through day 47.

The collagen hydrolysate used in Example 1 has the same composition as used in the clinical study in Example 3 (Table 2).

Treatment is started 4 days after the induction of PICS. The CH or vehicle is administered by daily oral gavage for a duration of 7 weeks (day 12-47).

In a follow-up study, the efficacy of group 3 (1.8 g/kg CH) is compared to that of fluoxetine (20 mg/kg) and whey protein (high in cysteine, 1.8 g/kg), administered by the same method.

Assessment of PICS

PICS sub-component #1 was determined with a grip strength meter (UGO Basile) to measure the forelimb grip strength, and the maximal force (g) was recorded. The mouse was pulled slightly backward by the tail while the forelimbs grasped the bar, which triggers a counter pull and automatically records the peak tension. Measurements were replicated in triplicate, and the maximum force of the three measurements were recorded. Data are quantified in % of grip loss.

PICS sub-component #2 relates to PICS-associated changes in the level of anxiety. Mice were subjected to an open-field test (Ethovison XT, Noldus) with an open field of 46×46×40 cm divided into peripheral and central zones. The time spent in the central and peripheral zone is recorded. PICS sub-component #2 was calculated as the ratio of the time spent in the center over the total movement time and expressed as a percentage of the total movement time. Lower time spent in the central region is indicative of greater anxiety levels.

PICS sub-component #3, #4, #5 relate to PICS-associated behavioral changes. The object recognition test was conducted using an open field comprised of a box 46×46×40 cm and a digital camera was used to record behavioral videos. Videos were recorded, and the time spent by mice with each object was calculated. First, the mice were allowed to explore and habituate to the empty open field box. Next, the test consists of two sessions (10 min each with 30 min intervals between each session). In the training session (acquisition phase), two similar objects were placed, and mice were allowed to explore them. In the test session (test phase), one object was replaced with a novel object. The interaction of the mouse with both objects (familiar and novel) was recorded. Exploratory activity and time spent sniffing each object during training and testing sessions were scored by Ethovision XT software. The percent discrimination index was calculated as 100× time spent exploring the novel object minus the time spent exploring the familiar object (Tnovel−Tfamiliar) divided by total exploration time (Tnovel+Tfamiliar). Index of habituation indicates familiar object recognition and is calculated (based on A Ennaceur et al. Behav Brain Res. 1988 Nov. 1; 31(1):47-5) as the difference between average time spent exploring the objects in training and exploring novel objects in a test phase.

The PICS parameters were investigated over a period of 3-7 weeks after the induction of PICS. Table 1 shows the PICS score as normalized to the "control" group.

Results are shown for a sample size of 9-11.

Results

FIG. 1 shows the PICS score in the "control", "PICS", "PICS+low dose CH" and "PICS+high dose CH" groups. It can be seen that overall PICS is reduced by ~38% in the "PICS+low dose CH" group and by ~23% in the "PICS+high dose CH" group, compared to the "PICS" group (i.e. without collagen hydrolysate). Thus, both CH doses are effective in ameliorating PICS.

Table 1 shows the improvement in individual PICS parameters in the "PICS+low dose CH" and "PICS+high dose CH" groups, compared to the "PICS" group. It can be seen that both doses overall improve the individual PICS sub-components.

TABLE 1

Improvement (%) in individual PICS parameters for the low dose and high dose CH groups, compared to the "PICS" group (without CH administration)

| PICS sub-component | Low dose CH | High dose CH |
|---|---|---|
| #1 | 15% | 15% |
| #2 | 43% | −14% |
| #3 | 78% | 84% |
| #4 | 47% | 27% |
| #5 | 19% | 25% |
| average | 40% | 28% |

The effects of high dose CH are compared to fluoxetine and whey proteins, i.e. agents with demonstrated efficacy in conditions related to PICS. Fluoxetine has been shown to offer neuroprotection in conditions of stress, emotion, and affective behaviours in mice with PICS-related symptoms (Wang et al. Aging (Albany NY). 2021 Feb. 22;13(6):8720-87360). It is therefore hypothesized that fluoxetine can ameliorate PICS by restoring mental and cognitive health in the PICS model. Whey protein has been suggested to promote healing and recovery in critically ill patients, e.g. by limiting muscle atrophy and promoting metabolic stability (Tsutsumi et al. JPEN J Parenter Enteral Nutr. 2015 July; 39(5):552-61). It is therefore hypothesized that fluoxetine can ameliorate PICS by restoring physical health in the PICS model.

As expected, in contrast to collagen hydrolysate, treatment with whey protein or fluoxetine leads to little/no improvement in PICS score. This shows that agents targeting only certain sub-components or individual symptoms of PICS cannot ameliorate PICS as a whole.

The PICS sub-component #1 was evaluated at week 1 and week 3-7 for all groups (6-time points). Mostly starting from week 5 an improvement in PICS sub-component #1 was seen. Similar timing effects were also seen for the other PICS sub-components.

Example 2: Effect of Collagen Hydrolysate Source and Molecular Weight

Objective

To investigate the single-dose bioavailability of collagen hydrolysate from different sources and of different mean molecular weight. It is considered that the ability of a collagen hydrolysate to ameliorate PICS is associated with this bioavailability.

Methods

Bioavailability was assessed by evaluating the uptake of free and peptide-bound hydroxyproline (Hyp) as marker amino acid. A randomized, double blind, cross-over clinical study was performed with healthy volunteers.

A single-dose of 10 g collagen hydrolysate was provided at low mean molecular weight (2000 Da). For the bovine collagen hydrolysate, a single-dose of 10 g was provided of either low mean molecular weight (2000 Da, "LMW") or high mean molecular weight (5000 Da, "HMW"). Blood was sampled for analysis over a period of 6 hours after collagen hydrolysate ingestion.

Results

FIG. 2 shows the concentration-time curves of the free Hyp response (A) or total Hyp response (B) after intake of study products.

It was found that, by intake of 10 g of the collagen hydrolysate, free Hyp concentrations in plasma ($\Delta C_{max}$) were greatly increased with an average factor of 7.2 for fish, 9.9 for porcine and 6.2 for both bovine low molecular weight (LMW) and high molecular weight (HMW) collagen hydrolysate. With respect to the bioavailability of free Hyp, there were no significant differences between the incremental area under the curve (iAUC) of the investigated products. In addition, Hyp content in blood samples was determined after total hydrolysis. Significantly higher concentrations of total Hyp were determined comparing the iAUC of free and total Hyp. The total Hyp concentrations in plasma ($\Delta C_{max}$) were also greatly increased for either fish and porcine collagen hydrolysate, and both for bovine collagen hydrolysate LMW and bovine collagen hydrolysate HMW.

Overall, the results show that the uptake of collagen hydrolysates in blood appears similar for collagen hydrolysates from the sources porcine, bovine and fish and also for hydrolysates with a relatively high average molecular weight (5000 Da) and relatively lower average MW (2000 Da).

Example 3: PICS Clinical Study

Objective

Based on the findings of the PICS animal model, a clinical study is performed to verify the use of collagen hydrolysate in the prevention and/or treatment of PICS in a clinical setting. The aim is to study the effect of six weeks intervention of porcine collagen hydrolysate administration versus control (maltodextrin administration) on PICS after ICU stay.

Methods

Study Design

Randomized controlled (double-blind) trial in 72 ICU-patients >18 years old discharged from the ICU (minimum ICU stay of 72 h). One group receives twice daily 22 g porcine collagen hydrolysate (20 g proteins, 80 kcal), so in total 44 g (40 g proteins, 160 kcal) per day. The other group receives twice daily 21 g maltodextrin (0 g protein, 82 kcal), so in total 42 g (0 g protein, 164 kcal). Interventions are isocaloric. Collagen hydrolysate or maltodextrin is provided in the morning and the afternoon.

Investigational Product

The porcine collagen hydrolysate is provided in a powdered form. The powder contains approximately 97% protein of dry weight. The porcine protein supplement (per 100 g) contains, on average: 360 kcal, 0 g fats, 0 g carbs (of which 0 g sugar), 90 g proteins and 0 g fibers. The amino acid content can be found in Table 2 below. The collagen hydrolysate has an average molecular weight of ~1800 Da.

The control group will receive maltodextrin daily for six weeks. Maltodextrin is a polysaccharide, and it is also provided as a white powder. The intervention product consists of primary proteins and no carbs, and maltodextrin contains carbs and no proteins.

Maltodextrin (per 100 g) contains, on average: 390 kcal, 0 g fats, 97.5 g carbs (of which 8.8 g sugar), 0 g proteins and 0 g fibers. The collagen hydrolysate and maltodextrin have similar appearances and the doses provided in the study are isocaloric.

TABLE 2

Amino acid content of the collagen hydrolysate

| Amino acid | g/100 g protein | g/22.22 g protein | g/44.44 g protein |
|---|---|---|---|
| Alanine | 9.1 | 2.02202 | 4.04404 |
| Arginine | 8 | 1.7776 | 3.5552 |

TABLE 2-continued

Amino acid content of the collagen hydrolysate

| Amino acid | g/100 g protein | g/22.22 g protein | g/44.44 g protein |
|---|---|---|---|
| Aspartic acid | 5.1 | 1.13322 | 2.26644 |
| Glutamic acid | 10.1 | 2.24422 | 4.48844 |
| Glycine | 22.3 | 4.95506 | 9.91012 |
| Histidine | 1.6 | 0.35552 | 0.71104 |
| Hydroxylysine | 0.8 | 0.17776 | 0.35552 |
| Hydroxyproline | 10.2 | 2.26644 | 4.53288 |
| Isoleucine | 1.3 | 0.28886 | 0.57772 |
| Leucine | 2.8 | 0.62216 | 1.24432 |
| Lysine | 3.7 | 0.82214 | 1.64428 |
| Methionine | 0.9 | 0.19998 | 0.39996 |
| Phenylalanine | 2 | 0.4444 | 0.8888 |
| Proline | 14.3 | 3.17746 | 6.35492 |
| Serine | 3.4 | 0.75548 | 1.51096 |
| Threonine | 1.9 | 0.42218 | 0.84436 |
| Tyrosine | 0.5 | 0.1111 | 0.2222 |
| Valine | 2.3 | 0.51106 | 1.02212 |

Route of Administration

The collagen hydrolysate or maltodextrin is provided in powder form packaged in identical sachets. Each administration sachet contains 22 g, each maltodextrin sachet contains 21 g. Both powders are freely soluble so that they can be dissolved in liquids. For example, 10 g collagen hydrolysate can easily be dissolved in 200 ml of lemonade with just a little stirring, and even higher amounts are possible (more concentrated).

Assessment of PICS

PICS is assessed according to a measuring instrument of the local hospital, which uses a combination of the following parameters:

composite score consisting of handgrip strength (Jamar dynamometer);
muscle strength leg (HHD m. quadriceps fem);
muscle strength arm (HHD m. biceps brachii);
exercise capacity (6MWD);
handgrip strength (Jamar dynamometer);
muscle strength leg (HHD m. quadriceps fem);
muscle strength arm (HHD m. biceps brachii);
exercise capacity (6MWD);
lower extremity muscle strength (TCST);
CPAx;
MRCsum;
Health related quality of life (assessed by EQ-5D);
Barthel score;
Rockwood Clinical Frailty Scale.

Bioabsorption of Amino Acids

The time-course appearance of free glycine in the human plasma after the ingestion of the collagen hydrolysate was measured in six subjects hourly.

Outcome

The clinical study uses the same administration scheme as the PICS animal model in Example 1. The administration of collagen hydrolysate after ICU stay improves recovery from critical illness and prevents PICS from developing. From earlier clinical studies, the administration of collagen hydrolysate and the dose is considered safe (e.g. based on adverse events, lab creatinine, urea, CK, glucose, Hb, CRP). The clinical study confirms earlier results and collagen hydrolysate can be specifically used in ICU survivors to prevent and/or treat PICS in daily practice.

After ingestion of collagen hydrolysate, it was found that glycine levels increased to the maximum concentration at one hour time point. Subsequently, the glycine declines close to the base level over the course of several hours (FIG. 3). This observation suggests that one of the significant (abundant) amino acids absorbs quickly and is absorbed in and/or eliminated from the body over time.

The invention claimed is:

1. A method for improving the recovery of a subject after intensive care unit stay comprising administering a collagen hydrolysate to the subject, wherein the collagen hydrolysate is derived from one or more of porcine, bovine or fish and has an average molecular weight of no more than 5,000 Daltons (Da), and wherein improving the recovery of the subject after intensive care unit stay comprises prevention and/or treatment of post-intensive care syndrome (PICS).

2. The method according to claim 1, wherein the collagen hydrolysate is administered at 10-100 g total dose per day, based on the dry weight amount of the collagen hydrolysate.

3. The method according to claim 2, wherein the dosage regimen for collagen hydrolysate comprises administering collagen hydrolysate for at least 3 consecutive weeks after intensive care unit stay.

4. The method according to claim 2, wherein the dosage regimen for collagen hydrolysate comprises administration of collagen hydrolysate starting within 3 weeks after intensive care unit stay.

5. The method according to claim 2, wherein the dosage regimen for collagen hydrolysate comprises administering collagen hydrolysate at least once every day or at least once every other day.

6. The method according to claim 1, wherein the collagen hydrolysate has an average molecular weight of 1000-5000 Da.

7. The method according to claim 1, wherein the collagen hydrolysate has an average molecular weight of 1400-2200 Da.

8. The method of claim 1, wherein the collagen hydrolysate is derived from hydrolysis of porcine collagen.

9. The method according to claim 1, wherein the collagen hydrolysate is administered before, during, or after intensive care unit stay.

10. The method according to claim 1, wherein the collagen hydrolysate has an average molecular weight of 1600-2000 Da.

* * * * *